United States Patent
Sun et al.

(10) Patent No.: US 9,427,496 B2
(45) Date of Patent: Aug. 30, 2016

(54) METHOD FOR CREATING AN INTERNAL TRANSPORT SYSTEM WITHIN TISSUE SCAFFOLDS USING COMPUTER-AIDED TISSUE ENGINEERING

(75) Inventors: Wei Sun, Cherry Hill, NJ (US); Jae Hyun Nam, Broomall, PA (US)

(73) Assignee: Drexel University, Philadelphia, PA (US)

( * ) Notice: Subject to any disclaimer, the term of this patent is extended or adjusted under 35 U.S.C. 154(b) by 1750 days.

(21) Appl. No.: 11/358,358

(22) Filed: Feb. 21, 2006

(65) Prior Publication Data

US 2006/0195179 A1 Aug. 31, 2006

Related U.S. Application Data

(60) Provisional application No. 60/654,106, filed on Feb. 18, 2005.

(51) Int. Cl.
*A61F 2/28* (2006.01)
*A61L 27/52* (2006.01)
*A61L 27/38* (2006.01)
(Continued)

(52) U.S. Cl.
CPC ............... *A61L 27/52* (2013.01); *A61F 2/02* (2013.01); *A61L 27/38* (2013.01); *A61L 27/46* (2013.01); *A61L 27/48* (2013.01); *A61F 2240/00* (2013.01)

(58) Field of Classification Search
CPC ..................... A61F 2/0077; A61F 2002/0081; A61F 2002/0086
USPC ....... 424/423–426, 93.7, 443–444, 484, 486; 435/399, 174–182, 397; 623/23.72–23.76; 606/152
See application file for complete search history.

(56) References Cited

U.S. PATENT DOCUMENTS 3,997,396 A 12/1976 Delente
4,200,689 A 4/1980 Knazek et al.
(Continued)

FOREIGN PATENT DOCUMENTS

WO 2005057436 A1 6/2005

OTHER PUBLICATIONS

Jockenhoevel, S, et al. Fibrin gel—advantages of a new scaffold in cardiovascular tissue engineering. European Journal of Cardithoracis Surgery. 2001; 19: 424-430.
(Continued)

*Primary Examiner* — Tuan V Nguyen
(74) *Attorney, Agent, or Firm* — Saul Ewing LLP; Kathryn Doyle, Esq.; Brian R. Landry, Esq.

(57) ABSTRACT

An artificial tissue including an internal mass transport network having a plurality of channels, wherein the channels are designed to substantially mimic naturally occurring vascular network and a method for creating an internal transport system within a tissue scaffold to improve circulation, diffusion, and mass transport properties by utilizing computer-aided tissue engineering (CATE). The artificial tissue has the internal mass transport network of channels embedded, deposited, or molded within a scaffold, wherein the channels are made from a biodegradable transporting material and the scaffold is made from a scaffold material. The artificial tissue of the invention includes a basic circulatory system embedded within the tissue scaffold. This system provides mass transport throughout the entire scaffold and degrades after the new circulatory system develops.

8 Claims, 8 Drawing Sheets

(51) Int. Cl.
  *A61L 27/46* (2006.01)
  *A61L 27/48* (2006.01)
  *A61F 2/02* (2006.01)

(56) References Cited

U.S. PATENT DOCUMENTS

| | | | |
|---|---|---|---|
| 5,081,035 | A | 1/1992 | Halberstadt et al. |
| 5,330,911 | A | 7/1994 | Hubbell et al. |
| 5,523,228 | A | 6/1996 | Ingram et al. |
| 5,549,674 | A | 8/1996 | Humes et al. |
| 5,736,399 | A * | 4/1998 | Takezawa et al. ............ 435/399 |
| 5,976,780 | A | 11/1999 | Shah |
| 6,001,585 | A | 12/1999 | Gramer |
| 6,001,643 | A | 12/1999 | Spaulding |
| 6,008,049 | A | 12/1999 | Naughton et al. |
| 6,027,744 | A | 2/2000 | Vacanti et al. |
| 6,103,255 | A | 8/2000 | Levene et al. |
| 6,129,761 | A | 10/2000 | Hubbell |
| 6,139,574 | A | 10/2000 | Vacanti et al. |
| 6,143,293 | A | 11/2000 | Weiss et al. |
| 6,171,610 | B1 * | 1/2001 | Vacanti et al. ................ 424/426 |
| 6,176,874 | B1 | 1/2001 | Vacanti et al. |
| 6,333,194 | B1 | 12/2001 | Levy et al. |
| 6,334,968 | B1 | 1/2002 | Shapiro et al. |
| 6,337,198 | B1 | 1/2002 | Levene et al. |
| 6,340,360 | B1 | 1/2002 | Lyles et al. |
| 6,372,244 | B1 | 4/2002 | Antanavich et al. |
| 6,423,252 | B1 | 7/2002 | Chun et al. |
| 6,454,811 | B1 | 9/2002 | Sherwood et al. |
| 6,455,311 | B1 | 9/2002 | Vacanti |
| 6,525,145 | B2 | 2/2003 | Gevaert et al. |
| 6,534,084 | B1 | 3/2003 | Vyakarnam et al. |
| 6,537,567 | B1 | 3/2003 | Niklason et al. |
| 6,547,994 | B1 | 4/2003 | Monkhouse et al. |
| 6,623,687 | B1 | 9/2003 | Gervasi et al. |
| 6,632,651 | B1 | 10/2003 | Nevo et al. |
| 6,642,363 | B1 | 11/2003 | Mooney et al. |
| 6,692,761 | B2 | 2/2004 | Mahmood et al. |
| 6,713,079 | B2 | 3/2004 | Usala |
| 6,730,252 | B1 | 5/2004 | Teoh et al. |
| 6,730,298 | B2 | 5/2004 | Griffith-Cima et al. |
| 6,730,315 | B2 | 5/2004 | Usala et al. |
| 6,772,026 | B2 | 8/2004 | Bradbury et al. |
| 6,949,252 | B2 | 9/2005 | Mizuno et al. |
| 2006/0036331 | A1 * | 2/2006 | Lu et al. .................... 623/23.51 |

OTHER PUBLICATIONS

Bhatia, S. N., et al. Tissue engineering at the microscale. Biomedical Microdevices. 1999; 2:2, 131-144.
Poncelet, D., et al. Formation of microgel beads by electric dispersions. American Institute of Chemical Engineers. 1999; 45(9): 2018-2023.
Vozzi, G., Microsyringe-based deposition of two-dimensional and three-dimensional polymers scaffolds with a well-defined geometry for application to tissue engineering. Tissue Engineering. 2002; 8(6): 1089-1098.
Freed, L. E., et al. Culture of organized cell communities. Advanced Drug Delivery Reviews. 1998; 33: 15-30.
Shachar, et al. Cardiac tissue engineering, ex-vivo: design principles in biomaterials and bioreactors. Heart Failure Reviews. 2003; 8: 271-276.
Abukawa, H., et al. Formation of a mandibular condyle in vitro by tissue engineering. J Oral Maxillofac Surg. 2003; 61: 94-100.
Grogan, S. P., et al. A static, closed and scaffold-free bioreactor system that permits chondrogenesis in vitro. Osteoarthritis and Cartilage. 2003; 11: 403-411.
Knazek R.A., et al. Cell culture on artificial capillaries: an approach to tissue growth in vitro. Science. 1972; 178: 65-67.
Freshney, I.R. Culture of animal cells: a manual of basic technique, 4th ed. John Wiley & Sons, Inc.: New York. 2000; p. 92.
Takezawa, T. A strategy for the development of tissue engineering scaffolds that regulate cell behavior. Biomaterials. 2003; 24: 2267-2275.
Takezawa, T., et al. Mass transport via naturally branched scaffolds maintains viability of a reconstituted model of connective tissue. Tissue Engineering. 1997; 3(4): 329-343.
Weiss, L.E., et al. Shape deposition manufacturing of heterogeneous structures. Journal of Manufacturing Systems. 1997; 16(4): 239-248.
Xiong, Z., et al. Fabrication of porous scaffolds for bone tissue engineering via low-temperature deposition. Scripta Materialia. 2002; 46:771-776.
Yan, Y., et al. Layered manufacturing of tissue engineering scaffolds via multi-nozzle deposition. Materials Letters. 2003; 57:2623-2628.
Landers, R., et al. Desktop manufacturing of complex objects, prototypes and biomedical scaffolds by means of computer-assisted design combined with computer-guided 3D plotting of polymers and reactive oligomers. Macromol Mater Eng. 2000; 282:17-21.
Landers, R., et al. Desktop manufacturing and biofunctional processing. Kunststoffe/plast Europe 2001; 91(12): 21-23.
Landers, R., et al. Rapid prototyping of scaffolds derived from thermoreversible hydrogels and tailored for applications in tissue engineering. Biomaterials. 2002; 23:4437-4447.
Calvert, P., et al. Solid freeform fabrication of organic-inorganic hybrid materials. Materials Science and Engineering. 1998; C6:167-174.
Vozzi, G., et al. Microfabricated PLGA scaffolds: a comparative study for application to tissue engineering. Materials Science and Engineering. 2002; C20:43-47.
Vozzi, G., et al. Fabrication of PLGA scaffolds using soft lithography and microsyringe deposition. Biomaterials. 2003; 24:2533-2540.
Ang, T.H., et al. Fabrication of 3D chitosan-hydroxyapatite scaffolds using a robotic dispensing system. Materials Science and Engineering. 2002; C20:35-42.
Khalil, S., et al. Multi-nozzle deposition for construction of 3D biopolymer tissue scaffolds. Rapid Prototyping Journal. 2005; 11(1):9-17.
Wang, F., et al. Precision extruding deposition and characterization of celluar poly-e-caprolactone tissue scaffolds. Rapid Prototyping Journal. 2004; 10(1):42-49.
Reischmann, M., et al. Prototype implementation of an assembly system for tissue engineered constructs. Electrotechnik and Informationstechnik. 2002; 718:248-252.
Darling, A.L., et al. Scaffold informatics: Multi-material strategies for tissue scaffolds. Poster Presentation for Proceedings of the 30th Annual Northeast Bioengineering Conference, Western New England College, Springfield, MA. Apr. 17-18, 2004.
Darling, A., et al. Scaffold informatics: tissue scaffolds based on imaging data. Poster Presentation for Proceedings of Focus on Microscopy Conference 2004. Philadelphia, Apr. 4-5, 2004.
Khalil, S., et al. Multi-nozzel biopolymer deposition and freeform fabrication of tissue scaffolds. Poster Presentation for Proceedings of the 14th Interdisciplinary Research Conference on Biomaterials, Limoges, France. Mar. 25-26, 2004.
Khalil, S., et al. Biopolymer deposition for freeform fabrication of tissue engineered scaffolds. Poster Presentation for Proceedings of the 30th Annual Northeast Bioengineering Conference, Western New England College, Springfield, MA. Apr. 17-18, 2004.
Calvert, P., et al. Freeform fabrication of hydrogels. Acta Materialia. 1998; 46(7): 2565-2571.
Lee, K.Y., et al. Hydrogels for Tissue Engineering. Chemical Reviews. 2001; 101(7).
Kweon, H.Y., et al. A novel degradable polycaprolactone networks for tissue engineering. Biomaterials. 2003; 24:801-808.
Stevens, M.M., et al. A rapid-curing alginate gel system: utility in periosteum-derived cartilage tissue engineering. Biomaterials. 2004; 25:887-894.
Neidert, M.R., et al. Enhanced fibrin remodeling in vitro with TGF-b1, insulin, and plasmin for improved tissue equivalents. Biomaterials. 2002; 23:3717-3731.

(56) References Cited

OTHER PUBLICATIONS

Ng, K.W., et al. In vitro characterization of natural and synthetic dermal matrices cultured with human dermal fibroblasts. Biomaterials. [2004; in press].

Khor, E., et al. Implantable applications of chitin and chitosan. Biomaterials. 2003; 24:2339-2349.

Drury, J.L., et al. Hydrogels for tissue engineering: scaffold design variables and applications. Biomaterials. 2003; 24:4337-4351.

Vacanti, J.P., et al. Tissue engineering: The design and fabrication of living replacement devices for surgical reconstruction and transplantation. Lancet. 1999; 354:32-34.

Leong, K.F., et al. Solid freeform fabrication of three-dimensional scaffolds for engineering replacements tissues and organs. Biomaterials. 2003; 42(13):2363-2378.

Hoffman, A.S. Hydrogels for biomedical applications. Advanced Drug Delivery Reviews. 2002; 43:3-12.

Ciapetti, G., et al. Osteoblast growth and function in porous poly e-caprolactone matrices for bone repair: a preliminary study. Biomaterials. 2003; 24:3815-3824.

Zein, I., et al. Fused deposition modeling of novel scaffold architectures for tissue engineering applications. Biomaterials. 2002; 23:1169-1185.

* cited by examiner

METHOD FOR CREATING AN INTERNAL TRANSPORT SYSTEM WITHIN TISSUE SCAFFOLDS USING COMPUTER-AIDED TISSUE ENGINEERING

CROSS-REFERENCE TO RELATED APPLICATIONS

This patent application claims the benefit of priority under 35 U.S.C. §119(e) from U.S. Provisional Patent Application Ser. No. 60/654,106, filed on Feb. 18, 2005. The entire content of the above-referenced patent application is herein incorporated by reference in its entirety.

BACKGROUND OF THE INVENTION

Field of Invention

This invention relates to artificially created tissues and methods of making the same, specifically, the invention relates to tissues with improved mass transport capabilities.

Description of Related Art

The shortage of organs for organ transplantation is a serious medical issue. The aging population continues to grow due to several factors such as, for example, the aging of the baby boomers population, improved lifesaving medical techniques and drugs, and a rise of average life expectancy. Tissue engineering is one of the avenues scientists explore to create various artificial organs. One of the major shortcomings of currently available artificial organs is inability to provide sufficient flow of nutrients, transport cells, and a removal of waste to support the growths of cells and development of tissues. Some tissue scaffolds are seeded with cells and implanted in vivo. They rely upon the infiltration and development of natural blood vessels into the scaffold to keep the cells alive. However, these processes may take too long and result in the death of cells, especially those cells located within the interior of the scaffold, wherein cells are starved for nutrients due to the limitations of diffusion.

Prior attempts to improve the flow include creating bioreactors to develop the cells within the tissue scaffold in vitro first, and implanting the tissue construct at a later stage of development.

Many different types of bioreactors have been designed to improve mass transport [1]. Some of the basic types of bioreactors are spinner flasks, various types of rotating cell culture systems (RCCS), and perfusion systems [2]. Cells with higher metabolisms have different requirements from cells with less of a need for mass transport. For example, a rotational, oxygen-permeable bioreactor system (ROBS) was used to culture osteoblasts [3] and chondrocytes [4]. Given the avascular nature of cartilage, such approach would not work for cells with greater metabolic requirements.

The general problem with many of known scaffolds is that the tissue constructs are still very small in size, i.e., only a few millimeters in diameter, and even less in depth for cells having higher metabolic requirements. Larger tissue constructs could be formed, provided that they could be vascularized quickly enough to prevent necrosis in tissue's interior. The creation of a circulatory system is vital for successful in vitro organogenesis.

Further, bioreactors are unnatural environments that do not reflect the conditions of living systems. Cells may be exposed to turbulent flows, which are not conductive for proper cellular development. Numerous inventors have tried to control the environmental conditions to improve cell culture conditions, see for example, U.S. Pat. No. 5,523,228 to Ingram, et al. and U.S. Pat. No. 6,001,643 to Spaulding.

Inventors have tried to imitate nature to help create a better environment for cell culture. Artificial capillaries have been described by Knazek, et al. [5] and Knazek et al., in U.S. Pat. No. 4,200,689 using hollow polymeric fibers that were permeable to gases. However, the problems with such structures include biocompatibility, implantation into a living organism, and limits to the space available for cell growth and expansion. Others have also explored hollow fiber systems and bioreactors (see, for example, U.S. Pat. No. 3,997,396 by Delente, U.S. Pat. No. 5,081,035 by Halberstadt et al., U.S. Pat. No. 5,549,674 by Humes, et al., and U.S. Pat. No. 6,001,585).

Pulsating flow systems have been created (U.S. Pat. No. 6,632,651 by Nevo, et al.) for growing cells in tissue scaffolds to mimic in vivo conditions. However, the circulatory mechanisms were external to the scaffold. There was no internal circulatory system built within the scaffold itself. Living systems have internal circulatory systems. Current tissue scaffolds do not provide for internal circulatory systems filled with materials for improving circulation.

Most tissue scaffolds rely upon diffusion for supplying cells with nutrition. Diffusion is highly limited. For static culture, the depth of the medium should only be 2-5 mm for adequate diffusion of oxygen to the cells [6]. In normal tissue, cells are generally within 200 micrometers at most from their blood supply.

With the current state of technology for tissue scaffolds, methods for improving diffusion generally do not go beyond creating simple channels and pores (see U.S. Pat. No. 6,534,084 to Vykarnam, U.S. Pat. No. 6,423,252 to Chun, et al.) or improving pore structure (see U.S. Pat. No. 6,103,255 to Levene et al., U.S. Pat. No. 6,537,567 to Niklason et al. describing various possibilities for a tissue engineered construct). However, these methods adhere to the traditional paradigm of transport through lumens, tubes, and fibrous meshes. U.S. Pat. No. 6,455,311 by Vacanti describes etching or creating channels and lumens on various substrates and in three-dimensions using various manufacturing techniques. Again, the mindset is still the same. Levene, et al. U.S. Pat. No. 6,337,198 describes their invention of a porous scaffold with an interconnected system of open pores to promote diffusion.

The conventional paradigm is based on using macropores, channels and microchannels as the primary means of diffusion. The problem with these scaffold designs is that channels can become occluded as cells grow and lay down extracellular matrix, thus choking off the flow of nutrients resulting in cellular necrosis occurring within the interior of the scaffold. Currently, it is very difficult to keep a large tissue construct adequately supplied with enough oxygen and nutrients, and to remove cell waste products from their local environment.

Hydrogels, such as alginates, have been used as cell scaffold materials. In the case of alginates, poor cell adhesion has been looked upon as a negative. Researchers have done experiments with chemical modification of alginates, such as adding RGD peptides or doing other chemical modifications to improve cell adhesion (Mooney, et al. in U.S. Pat. No. 6,642,363).

Hubbell, et al. in U.S. Pat. No. 5,330,911 describe the use of RGD, YIGSR, or REDV moieties to improve cell adhesion to surfaces, as well as utilizing PEO to prevent cell adhesion and clotting. Usala in U.S. Pat. No. 6,713,079 uses hydrogel matrix, such as collagen, to promote cell growth, infiltration, and vascularization to improve wound healing.

Hydrogels have been used for cell-encapsulation an example (see, for example, U.S. Pat. No. 5,976,780 to Shah). Hubbell in U.S. Pat. No. 6,129,761 describes the use of hydrogel-cell compositions in an injectable form. Griffith-Cima et al. in U.S. Pat. No. 6,730,298 use hydrogels as a method for cell delivery via encapsulation, and also shaping the injected gel using a mold. Others follow a similar pattern of using hydrogels for cell proliferation, encapsulation, and injection such as Usala, et al. in U.S. Pat. No. 6,730,315. Vacanti, et al. in U.S. Pat. No. 6,027,744 and Vacanti, et al. in U.S. Pat. No. 6,171,610 also use hydrogels as a scaffold material with cells embedded within the hydrogel. The diffusive properties of the hydrogel allow mass transport to occur to and from the cell, thereby keeping the cell alive. However, this also follows the basic idea of cell encapsulation, and cells are suspended within the hydrogel.

They essentially follow the conventional paradigm of using hydrogels for encapsulation and scaffolding for cells. The thought of using the hydrogel as an acellular material designed to function other than as a support or encapsulating matrix is not considered. Mahmood et al. in U.S. Pat. No. 6,692,761 utilize the basic property of hydrogels in allowing diffusion of materials and nutrients. These diffusion properties of hydrogels have been utilized for drug delivery. Dextran hydrogels have been used for drug delivery (see U.S. Pat. No. 6,525,145 to Gevaert, et al.). Antanavich, et al. in U.S. Pat. No. 6,372,244 designed thin sheets of cellular implants to promote diffusion. Their invention was similar to cell encapsulation by alginate. Lyles et al. in U.S. Pat. No. 6,340,360 detailed an implant that used a biodegradable matrix to deliver drugs and biological factors via diffusion. Shapiro, et al. in U.S. Pat. No. 6,334,968 detailed their invention of an alginate sponge for use as a cell matrix, cell scaffold, and for delivery of therapeutic agents.

However, none of these inventions recognized the possibility of creating an artificial transport system utilizing the diffusion properties of hydrogels.

Naughton et al. in U.S. Pat. No. 6,008,049 devised a bioreactor that uses diffusion gradients to simulate a more natural method of supplying nutrients and removing wastes. Cells are seeded onto a mesh, but the mesh merely acts as a scaffolding and support structure, and is not actively involved in transport functions.

Mizuno et al. in U.S. Pat. No. 6,949,252 utilized the capillary effect of a collagen sponge in order to seed the matrix with cells; however, the capillary effect was not designed to provide for a method of mass transport. The capillary effect was to help promote cell seeding.

Takezawa and Takezawa, et al. utilized readily available fibrous meshes to function as a capillary-like network for mass transport. They cultured fibroblasts on a cotton gauze mesh coated with collagen. They used its absorptive capabilities to help circulate fluid throughout the culture by connecting it to a peristaltic pump [7, 8]. In addition, they utilized the roots of a rice plant as a novel scaffold for growing fibroblasts [8]. Takezawa, et al. in U.S. Pat. No 5,736,399 described the use of natural or synthetic threads or meshes to act as a means of improving diffusion within a three-dimensional cell culture. A device could be physically connected to the network to improve transport of culture media to the cells. This method has a disadvantage in that it would be difficult to integrate the diffusive mesh into a tissue scaffold. Also, gels were used as a coating for the mesh.

Layered manufacturing techniques have been applied to the field of biology. This has resulted in much research being conducted within the field of computer-aided tissue engineering (CATE).

Reischmann and Weiss, et al. have described a method for building bone tissue scaffolds using laminated sheets of material and stacking them together [9, 10]. Yan and Xiong et al. have disclosed the concept of using layered manufacturing methods and multi-nozzle deposition extrusion and jetting processes [11, 12]. R. Landers et al. have also devised a SFF method using a syringe-based system to dispense liquids, which is suited for working with biological materials such as cells and hydrogels [13, 14, 15]. Calvert et al. have devised a syringe-based system for the extrusion of hybrid polymer materials embedded with glass using layered SFF manufacturing [16]. Vozzi et al. have devised a microsyringe deposition system [17, 18]. Ang et al. created a single-nozzle, automated extrusion system that can utilize basic STL files [19]. U.S. Pat. No. 6,139,574 (Vacanti et al. Oct. 31, 2000) discloses vascularized tissue regeneration matrices formed by solid free form fabrication techniques. U.S. Pat. No. 6,143,293 (Weiss, et al. Nov. 7, 2000) discloses assembled scaffolds for three dimensional cell culturing and tissue generation. U.S. Pat. No. 6,027,744 and U.S. Pat. No. 6,171,610 (Vacanti, et al. Feb. 22,2000 and Vacanti, et al. Jan. 9,2001) describe guided development and support of hydrogel-cell compositions. U.S. Pat. No. 6,176,874 (Vacanti, et al. Jan. 23, 2001) discloses vascularized tissue regeneration matrices formed by solid free form fabrication techniques. U.S. Pat. No. 6,454,811 (Sherwood, et al. Sep. 24, 2002) discloses composites for tissue regeneration and methods of manufacture thereof. This method primarily focuses on 3DP for tissue engineering. U.S. Pat. No. 6,547,994 (Monkhouse, et al. Apr. 15, 2003) describes a process for rapid prototyping and manufacturing of primarily drug delivery systems with multiple gradients, mostly involving the 3DP technique. U.S. Pat. No. 6,623,687 (Gervasi, et al. Sep. 23,2003) describes a process for making three-dimensional objects by constructing an interlaced lattice construct using SFF to create a functional gradient material.

Tissue scaffolds are limited by a lack of diffusion and circulation. The current state of technology generally relies upon interconnected channels and pores. Attempts to improve circulation are done externally using bioreactors to improve the flow of culture medium around the scaffold. Passive transport, such as a diffusion process, has an advantage in that it does not require the presence of a mechanical apparatus associated with bioreactors and perfusion pumps. Artificial methods for creating internal, diffusive meshes have been devised; however, their integration into a tissue scaffolds is too complex and does not provide reliable and consistent results. However, the presently known scaffolds are still diffusion limited internally and large scaffolds can have necrotic cores.

Thus, despite the foregoing developments, there is still a need in the art for artificial tissues having an improved internal transportation network.

All references cited herein are incorporated herein by reference in their entireties.

BRIEF SUMMARY OF THE INVENTION

The present invention includes an artificial tissue comprising an internal mass transport network having a plurality of channels, wherein the channels are designed to substantially mimic naturally occurring vascular network and a method for creating an internal transport system within a tissue scaffold to improve circulation, diffusion, and mass transport properties by utilizing computer-aided tissue engineering (CATE).

The artificial tissue of the invention has the internal mass transport network of channels embedded, deposited, or molded within a scaffold, wherein the channels are made from a biodegradable transporting material and the scaffold is made from a scaffold material. Thus, the artificial tissue of the invention has a basic circulatory system embedded within the tissue scaffold. This system provides mass transport throughout the entire scaffold and degrades after the new circulatory system develops.

The artificial tissue of the invention can be used as scaffolds, artificial organs, and artificial implants in tissue engineering and manufacturing tissue scaffolds, artificial organs, and artificial implants.

In certain embodiments, the artificial tissue further includes a transpiratory system Also provided is a method for making the artificial tissue.

BRIEF DESCRIPTION OF SEVERAL VIEWS OF THE DRAWINGS

The invention will be described in conjunction with the following drawings in which like reference numerals designate like elements and wherein:

FIG. 1A is a step demonstrating multilayered deposition process using a first deposition nozzle depositing biodegradable transport material (shown herein in red) and a second deposition nozzle deposition scaffold material (shown herein in green);

FIG. 1B is a step showing the building of the scaffold in a layer-by-layer fashion by using multiple nozzles to deposit materials;

FIG. 1C is a step showing the completed scaffold with the integrated mass transport network built into the scaffold;

FIG. 1D is a phase where the biodegradable mass transport network starts to break down, while, vascularization of the scaffold increases; and FIG. 1E is a final phase where the artificial tissue is now completely vascularized and does not require the mass transport network to sustain cell viability.

FIGS. 2A and 2B is a scheme that illustrates a method for using transpiration to improve circulation throughout the scaffold, wherein FIG. 2A is an example of a scaffold with two regions, a lower region where cell and tissue will grow and an upper region that serves to pull nutrients throughout the hydrogel network, and FIG. 2B is an illustration of the scaffold being submerged into cell culture medium with the upper region being left exposed to the air.

DETAILED DESCRIPTION OF THE INVENTION

The invention was driven by a desire to develop an artificial tissue having improved mass transport capabilities which comprises an artificial internal mass transport network of channels that substantially mimics naturally occurring vascular network and a method of making such artificial tissue. The present invention includes an artificial tissue comprising an artificial internal mass transport network having a plurality of channels, wherein the channels are designed to substantially mimic naturally occurring vascular network. The artificial tissue of the invention has the internal mass transport network of channels embedded, deposited, or molded within a scaffold, wherein the channels consist of a biodegradable transporting material and the scaffold is made from a scaffold material. Thus, the artificial tissue of the invention has a basic circulatory system embedded within the tissue scaffold. This system provides mass transport throughout the entire scaffold and degrades after the new circulatory system develops.

The biodegradable transporting material are materials which preferably have limited cell retention capabilities and are capable of facilitating transport of nutrients to cells located on the scaffold material and degrading when the vascular system of the artificial tissue fully develops.

Non-limiting examples of the biodegradable transporting material are hydrogels. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate (HEMA), which are crosslinked, ionically bound, or bound block copolymers such as PLURONICS® or TETRONIC®, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In a preferred embodiment, the hydrogel comprises alginate to function as a diffusive network. Alginate's lack of cell adhesion and interaction is generally considered to be a negative; however, we utilize this "disadvantage" to create obstruction free zones that prevents clogging of the hydrogel network by cells and their deposited matrix. Differently from previously known systems utilizing porous structures for transport, the diffusive network of this invention is filled with hydrogel and optionally of other auxiliary materials.

Figures 1A, 1B, 1C, 1D, 1E:
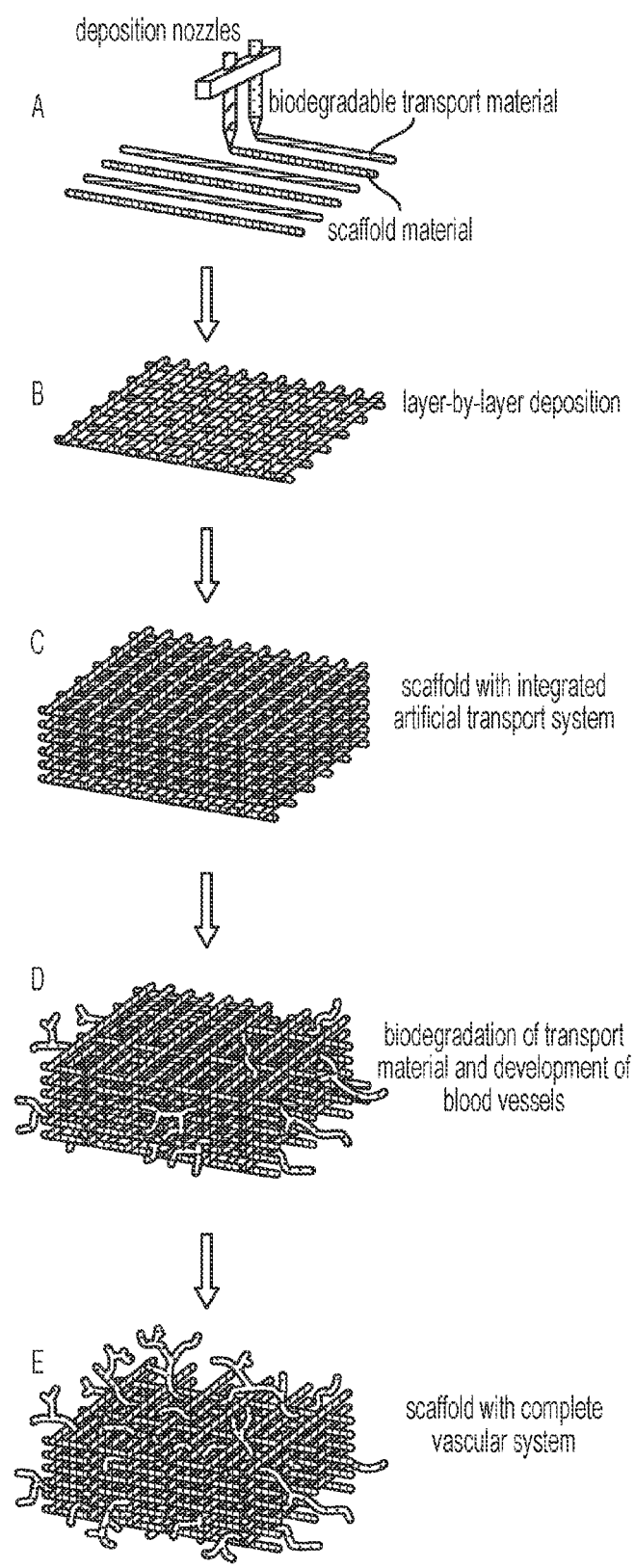
FIGS. 1A-1E are schemes that illustrate the coordinated degradation of the temporary transport network and the growth of natural blood vessels.

The biodegradable transporting material's composition can be altered to control its degradative properties. The biodegradation of the temporary circulatory network would be timed to coincide with the growth and development of blood vessels in the artificial tissue. As the tissue construct develops and its natural vascular system grows, the temporary circulatory system breaks down. In the early stage, the hydrogel network provides the main supportive functions for mass transport (see FIG. 1C). During the intermediate stage, both neovascularization and the degrading hydrogel network provide mass transport (see FIG. 1D). In the final stage, the artificial hydrogel network has degraded away, and natural blood vessels now provide all of the mass transport functions (see FIG. 1E). This invention solves the problem of neovascularization for in vivo implants. This also works in vitro as a more efficient method for improved circulation as compared to current types of bioreactors or static cell culture techniques.

In certain embodiments, the composition of the hydrogel is modified to selectively filter and allow the diffusion of desired particles. For example, denser hydrogel with more crosslinkages would hinder passage of larger macromolecules. The addition of charged moieties could be used to allow the selective passage of charged molecules and ions. In addition, chemical surface modification could be used to promote cell-specific adhesion when desired.

Non-limiting examples of the scaffold material are poly (caprolactones), poly(lactic acid), PLGA, fibrin, collagen, hydroxyapatite, and other biologically useful materials. The scaffold materials are preferably biocompatible.

Preferred examples of hydrogel include alginate, collagen, chitosan, fibrin, hyaluronic acid, agar, polyethylene glycol and its copolymers, acrylamide-based polymers, acrylic acid-based polymers, and the scaffold material is a member selected from the group consisting of polycaprolactone, polyglycolic acid, polylactic acid, polyhydroxybutyrate, polypropylene and their co-polymers, fumarate tricalcium phosphate, and hydroxyapatite. The scaffold material can have a wide range of biodegradability, depending on the desired properties and purpose of the scaffold.

The scaffold material can also be combined with various additives to better suit the type of cell or tissue that is being used. For example, hydroxyapatite could be used when working with osteoblasts to create bone implant scaffolds. The scaffold could also be coated with proteins and receptors that facilitate cellular adhesion or migration onto the scaffold surface. Growth factors and other biologically active agents could also be included within the scaffold material.

Once the tissue scaffold is completed, mechanical components and systems could be connected to the artificial vascular system to improve circulation even further. Non-limiting examples of such systems are perfusion pumps, suction pumps, or pulsatile flow pumps. A source of controlled air flow and/or temperature could be used to regulate the rate of transpiration. Air flow and temperature parameters could be oscillatory to mimic pulsatile mass transport within the scaffold.

The completed scaffold can be seeded with cells and cultured in suitable medium. As an example, the scaffold could be seeded with fibroblasts and cultured using Eagle's Minimal Essential Medium supplemented with 10% fetal bovine serum. Other types of cells include but are not limited to myoblasts, endothelial cells, neuroblasts, chondrocytes, osteoblasts, hepatic cells, pancreatic cells, stem cells, and cells within various states of differentiation. The basic medium can be adjusted as needed with changes in supplementation. Antibiotics and antimycotics can also be added if required. ALAMARBLUE® staining and a cytofluorometer can be used to determine cell proliferation, as well as live/dead assays. Histological slides and optical and phase contrast microscopy can be used to characterize cells in the center of the scaffold, and to examine the amount of cell necrosis and infiltration.

Advantageously, the internal mass transport network of channels in the artificial tissue is a temporary construct that can biodegrade and is not cumbersome so that the artificial tissue can be used in vitro as well as implanted in vivo, unlike many bioreactor setups which consist of non-biodegradable parts, require large external mechanical systems, and cannot be implanted in vivo.

The artificial tissue of the invention can be made by different processes such as, for example, extrusion, polymerization, or by threading a pre-formed scaffold with the biodegradable transporting material.

In certain embodiments, the artificial tissue includes a tissue scaffold having an internal vascular system in a form of a hydrogel transportation network and utilizes layered manufacturing techniques to deposit the hydrogel network within the scaffold in three-dimensions. In certain embodiments, the artificial tissue of the invention is made by using a multi-nozzle extruding deposition system, wherein multiple nozzles extrude various filaments to form a scaffold containing the internal mass transport network of channels (see FIGS. 1A-D). A multi-nozzle extruding deposition system is described in Khalil S, Nam J, Sun W. Multi-nozzle Deposition for Construction of 3D Biopolymer Tissue Scaffolds. *Rapid Prototyping Journal* 2005; 11 (1): 9-17 and in a PCT Publication No. WO05057436A1 to Sun et al and U.S. national phase application based thereupon incorporated herein in their entireties.

Figure 6:
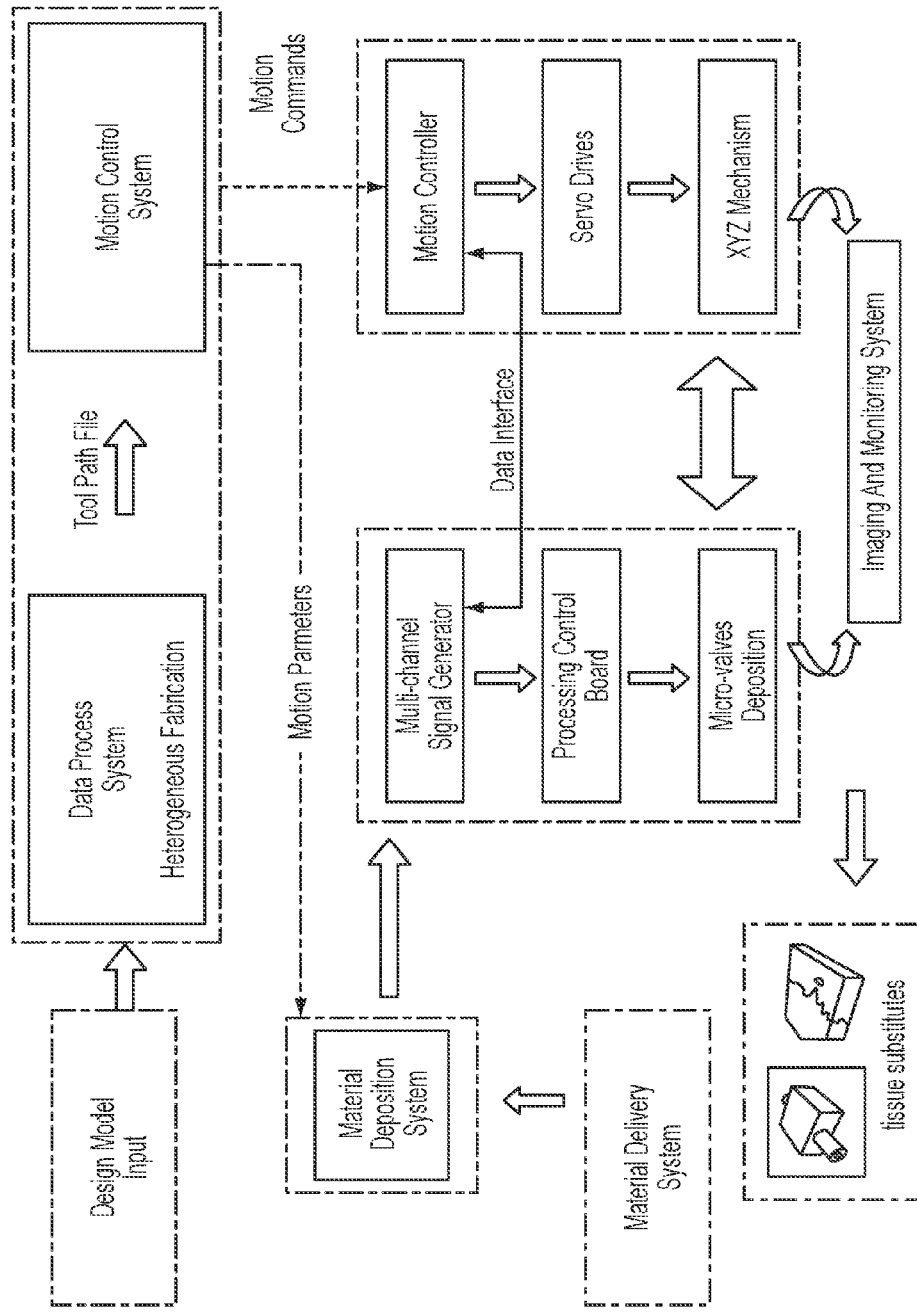
FIG. 6 is a scheme depicting a configuration of an exemplary biopolymer deposition system (as described in Khalil S, Nam J, Sun W. Multi-nozzle Deposition for Construction of 3D Biopolymer Tissue Scaffolds. *Rapid Prototyping Journal* 2005; 11 (1): 9-17)).
Figure 7:
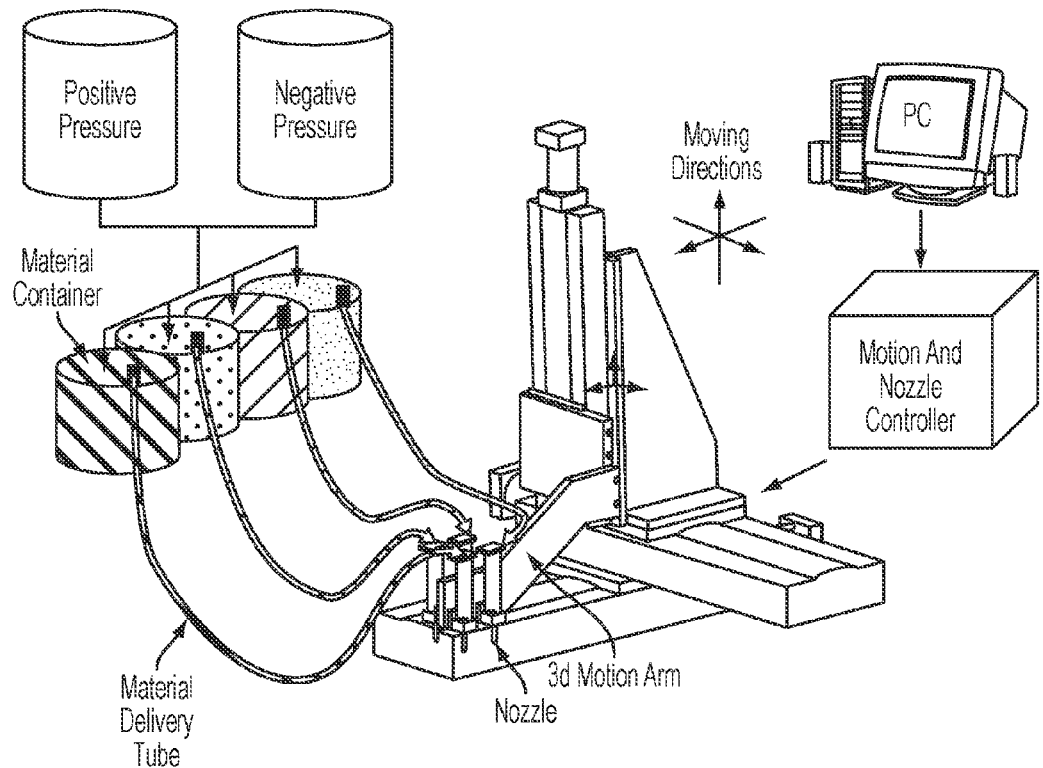
FIG. 7 is a scheme depicting a configuration of an exemplary system set-up for biopolymer depositions (Khalil S et al, 2005).
Figure 8:
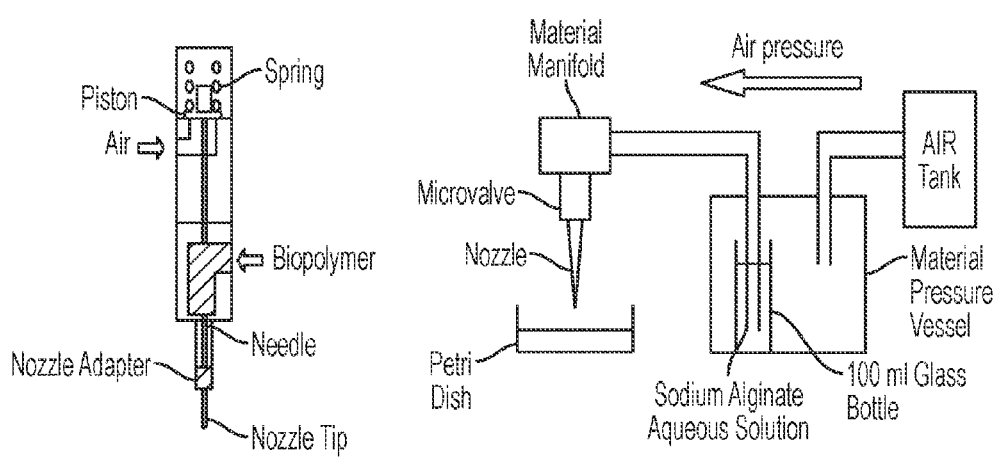
FIG. 8 is a schematic diagram of a pneumatic microvalve system (Khalil S et al, 2005).

The deposition process is biocompatible and occurs at room temperature and low pressures to reduce damage to cells. Other SFF manufacturing methods utilize harsh solvents, high pressures or temperatures, or post-processing methods that are not suited for working with bioactive materials. By contrast, our system is capable of, simultaneously, with the scaffold construction, depositing controlled amount of cells, growth factors, or other bioactive compounds with precise spatial position to form well-defined cell-seeded tissue constructs. This process may solve the problem of cell loading of preformed scaffolds which hitherto has been a significant barrier in tissue engineering. An information pipeline of multi-nozzle biopolymer deposition system for freeform fabrication of tissue constructs is shown in FIG. 6. As shown in FIG. 6, the data processing system processes the designed scaffold model and converts it into a layered process tool path. The motion control system is driven by the layered manufacturing technique; the material delivery system consists of multiple nozzles with different types and sizes, thus enabling the deposition of specified hydrogels with different viscosities for constructing 3D tissue scaffolds. Four types of the nozzles are used in the system: solenoid-actuated nozzles, piezoelectric glass capillary nozzles, pneumatic syringe nozzles, and spray nozzles, with size ranges varying from 30 to 500 mm. The system can continuously extrude hydrogel gels, or form hydrogels in single droplets with picoliter volumes. The multiple nozzle capability allows us to simultaneously deposit cells, growth factors, and scaffold materials, thus enabling the construction of heterogeneous scaffolds with bioactive compounds, or establishing functional gradient scaffolds with different mechanical/structural properties in different scaffold regions. The multi nozzle biopolymer deposition system consists of four different micro-nozzles: pneumatic microvalve, piezoelectric nozzle, solenoid valve, and precision extrusion deposition (PED) nozzle, as shown in FIG. 7. A material delivery system was assembled to supply the nozzles with the appropriate biopolymer. The system consisted of an air pressure supply both positive and negative, a material container or reservoir, and a material delivery tube. Each nozzle system had its independent parameters adjusted as required, such as the air pressure and biopolymer concentration. As an example, FIG. 8 shows a schematic diagram of pneumatic microvalve system. Pneumatic microvalve is a typical mechanical valve that opens and closes the valve via an applied air pressure and is regulated by a controller. The system could work in extrusion or droplet mode. In extrusion mode, the controller applies pressure to open the valve by lifting the piston against the spring that lifts the needle from the needle seat. The biopolymer material is then extruded out of the nozzle tip under an applied pressure that is adjusted through the material delivery system. The extrusion is ended when the controller shuts the valve by placing the needle back to the needle seat. The pneumatic valve could perform in droplet mode by repeating the continuous mode in a cyclic manner. Multiple pneumatic valves were simultaneously operated for performing heterogeneous deposition in the development of the 3D alginate scaffolds.

In certain embodiments, the artificial tissue of the invention is made by depositing a first filament comprising a biodegradable transporting material and a second filament comprising a scaffold material, wherein the first filament and the second filament are deposited in a pattern to form a plurality of layers of the artificial tissue, such that the biodegradable transporting material forms the internal mass transport network of channels within the scaffold of the artificial tissue. In certain embodiments, the first filament comprises more than one scaffold material and/or a plurality of first filaments. Further, the scaffold material can have additives added to it or co-extruded with it. Non-limiting examples of such additives are biomolecules, pharmacologically active agents, a component of substrate-ligand pair, compounds that control the rate of degradation, mechano-active elements, MEMS sensors and devices, and additives used to control material properties. Similarly, the transport material can also contain any, all, or more of the same types of additives to create the desired properties. By using different filaments, the artificial tissue of the invention can be tailored to best mimic naturally occurring tissue. Further, cells can also be mixed with the scaffold material.

The size and shape of the artificial tissue of the invention can vary depending on the application. The diameter of the transport filaments can be built on different scales ranging from millimeters to micrometers, preferably on a scale similar to their biological analogues, i.e., 8-10 μm for capillaries and capillary beds, and less than 100 μm for arterioles, and greater than 100 μm for arteries.

Figure 3:
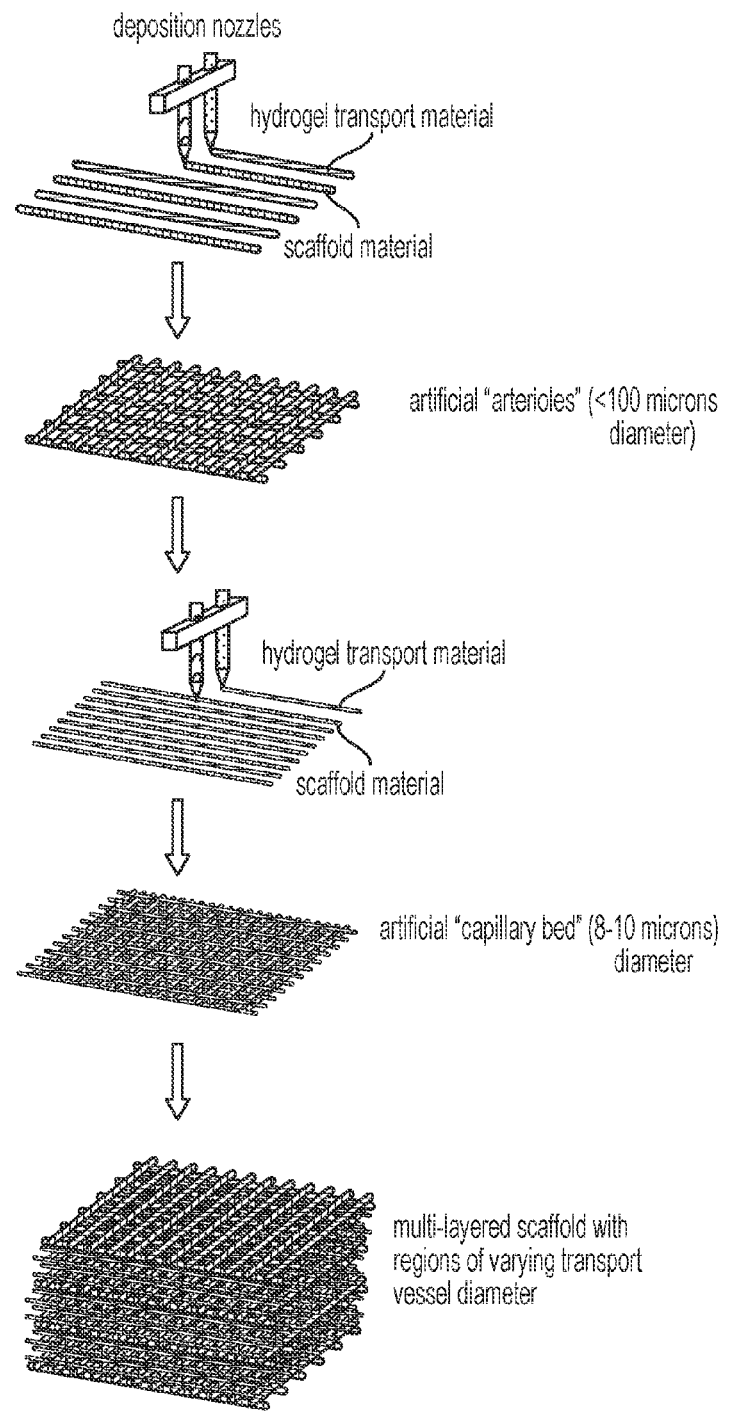
FIG. 3 is a scheme that illustrates making a scaffold with different sized transport vessels within the same scaffold. Although the illustration shows alternating layers, the scaffold can contain different sized vessels disposed within the same layer.

Sizes of the artificial transport vessels do not have to be uniform or have even flow properties. There are several different ways to do this, such as printing several vessels directly next to each other or overlapping to create a larger vessel, by using multiple nozzles that extrude or deposit different sized vessels, or by varying the operating parameters of the printhead, such as velocity, pressure, etc., during scaffold fabrication (see FIG. 3).

Figure 4:
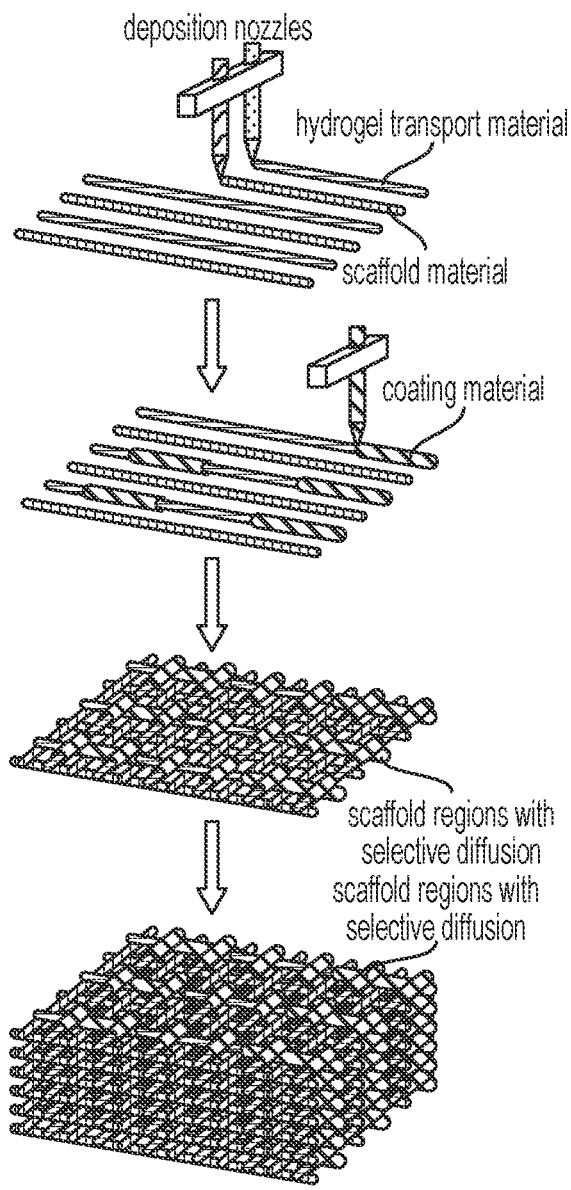
FIG. 4 is a scheme that illustrates making a scaffold with a nozzle that applies a coating to the scaffold filaments to alter the diffusion properties of the transport system. Coating material is shown herein in blue.

In certain embodiments, the artificial tissue of the invention is made by using an extra nozzle or nozzles to deposit a coating around the hydrogel transport system to improve its transport properties (see FIG. 4). The coating could be used to block the passage of water along parts of the vessel and transport network, and can thus be used to speed up the transport of fluids. The coating could also be used to alter the diffusive properties of the artificial internal mass transport network. The diffusive properties could be limited in some areas and increased in other areas. The diffusive properties could also be made more selective, with increased permeability to desired elements, such as biological proteins, or decreased permeability. Some non-limiting examples are charged coatings that selectively exclude or allow the passage of ions or charged molecules, coatings containing biological transport proteins, coatings containing receptor molecules and ligands that bind and facilitate transport of very specific cells and molecules, and hydrophilic and hydrophobic coatings. The coating can also contain extracellular matrix material, RGD-peptide sequences, and other bioactive materials designed to interact with cells.

Figure 5:
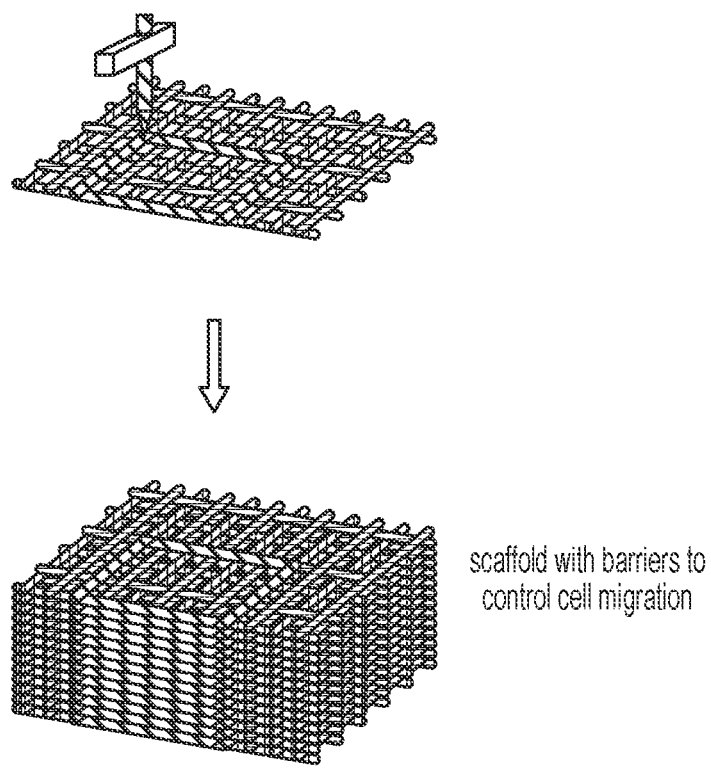
FIG. 5 is a scheme that illustrates making a scaffold with selective barriers to control cell migration behavior, thereby creating regions where certain types of cells and other biologically relevant agents can and cannot enter. The selective barriers are shown herein in blue.

In certain embodiments, the artificial tissue of the invention is made by using an extra nozzle or nozzles to deposit alginate or similar material to serve as a barrier to cell migration (see FIG. 5). This could be used to seal off or limit cell migration to certain regions of the scaffold. This could also be used to help keep cells contained within desired regions of the scaffold and help prevent overgrowth by more rapidly proliferating cell types.

In certain embodiments, the artificial tissue of the invention further comprises an additional circulatory mechanism to improve vascular circulation, which is based on transpiratory mechanism used by plants and trees (see FIG. 2). The passive hydrogel transport system described above can be coupled to a transpiration mechanism, as used in plants and trees, so as to function as a temporary circulatory system until sufficient vascularization is achieved. The inventors were first to appreciate the potential of the transpiration mechanism as applied to tissues. The simple mechanism of transpiration can supply enough oxygen and nutrients to grow plants and trees, so this method has the potential to grow organs.

Essentially, a developing organ or artificial tissue construct being grown will go through an initial "plant" phase where it relies upon transpiration as the primary means of circulation, then transition into a hybrid stage where transpiration and vascularization will supply the organ, then finally, the transpiratory mechanism will have degraded, and the vascular system will be sufficiently developed to handle the transport functions.

There are at least three methods of making transpiration circulatory system to be used with the artificial tissue of the invention.

Figures 2A, 2B:
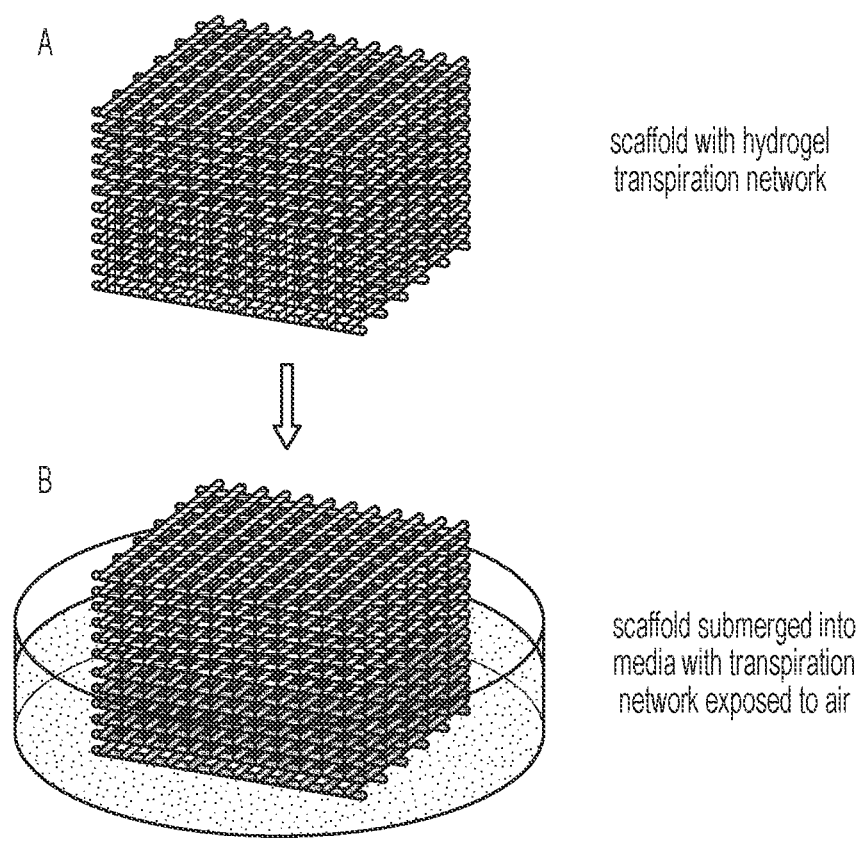

The first method requires creating a simple, grid-like, 3-D transpiration scaffold from hydrogel using a layered extrusion process, and then filling it halfway with fibrin gel (see FIGS. 2A-2B). The lower half of the scaffold is submerged within the medium and serves as the "roots". The upper half is exposed to the air, resulting in evaporation and transport of fluids through the hydrogel scaffold, thus functioning as the "leaves." The geometry of the alginate "leaves" can be varied to increase the surface area exposed to the air to maximize the circulation effect. As cells grow and begin to fill up the scaffold, the hydrogel channels will remain relatively free of cells and will be important for maintaining transport throughout the developing tissue structure.

The detailed hydrogel structure will be created through the use of solid freeform fabrication techniques. A hydrogel extrusion process will lay down the pattern of hydrogel to be used for the circulatory system. Fibrinogen and a combination of thrombin and calcium chloride would be used to create the fibrin gel for cellular attachment. The preferred hydrogel is alginate.

A second alternative method would be to use the PCL-hydrogel filament scaffold, but with much longer filaments. The filaments would extend out from the bottom of the scaffold-like roots, and the filaments that extend out from the top of the scaffold would intentionally be tangled up to form a "bushy" structure to maximize evaporation and transpiration by increasing the exposed surface area.

A third alternative method would be to deposit the alginate and fibrin scaffold materials by using multi-nozzle deposition. Essentially, the finished product would be similar to the first method; however, the alginate and fibrin would be deposited in a layer-by-layer fashion at the same time. The deposition methods can also be comprised of different delivery methods such as spray nozzles, piezoelectric nozzles, solenoid-actuated nozzles, and other methods of deposition.

The rate of transpiration can also be controlled during culture. Simple things such as altering the temperature and humidity will affect transpiration rate. In addition, it is possible to introduce a dynamic, cyclical component to the system that would simulate pulsatile flow. By using an oscillating airflow that flows past the "leaves," one can increase and decrease the rate of evaporation in a periodic manner. The major difference; however, is that circulation within the scaffold will be due to a negative pressure from transpiration, and not due to positive pressure, such as a pumping mechanism.

The invention will be illustrated in more detail with reference to the following Examples, but it should be understood that the present invention is not deemed to be limited thereto.

EXAMPLE 1

In this example, the hydrogel channel system are constructed from alginate. Cells do not adhere well to alginate. Ordinary, this property is viewed as a disadvantage. Inventors have discovered that, this property can be used to our advantage within a hybrid scaffold since it would keep the alginate channels clear of blockages, thereby maintaining an open network to improve circulation. A poly(caprolactone) (PCL) scaffold is created with the precise extruding deposition system (PED) [21] and sterilized using 70% ethyl alcohol and UV light. The alginate filaments are created by extruding sodium alginate or potassium alginate into a calcium chloride crosslinking solution using a pneumatic nozzle system.

The equipment is wiped down with ethyl alcohol and set up under a laminar flow hood. Ethyl alcohol is run through to sterilize the interior of the system. Sterile, filtered air is used to actuate the valve. The alginate and crosslinking solutions are sterilized using UV light or ethanol as required. All solutions are mixed under sterile conditions. The alginate filaments are deposited during the creation of the PCL scaffold to create the artificial tissue containing an internal mass transport network of alginate channels within the scaffold. An alternative embodiment includes creating the alginate filament separately, and then thread it through the pre-made PCL scaffold manually or via an automated system.

EXAMPLE 2

In this invention, the inventors utilize the unique manufacturing capabilities of 3D printing of multiple materials to optimize several aspects of tissue scaffolds simultaneously. Such parameters include mechanical properties, surface area available for cell attachment, material affinity for cell attachment, nutrient and gas transport efficiency, and biocompatibility. There has been a tendency in the community to investigate materials for these characteristics either singly or in homogenous mixtures [A20]. The use of 3D printing of multiple materials presents the option of combining specialist materials in a manner not achievable by mixing and casting. It is proposed that simultaneous deposition of four candidate materials can both improve the output of 3D tissue culture and gain greater control of cell growth and expression within the proposed scaffolds. A heterogeneous material printer could selectively lay down porosities for cell proliferation and transport, materials for cellular attachment, novel hydrogel diffusion networks to enhance transport, and degradative elements capable of releasing growth factor into a localized region. Inventors developed such a heterogeneous material 3D printer, dubbed the Heteroform printer, with these capabilities. The Heteroform printer was first described in a poster presentation in April, 2004 at AD-NEBE meeting (Darling et al., Heterogeneous Material Strategies for Tissue Scaffold Manufacture).

Figure 9:
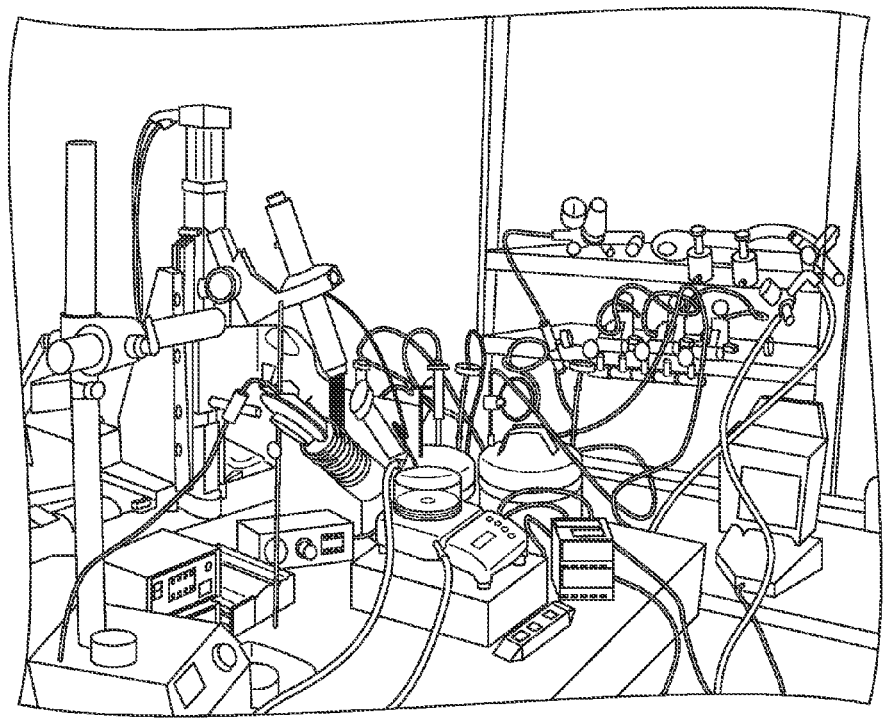
FIG. 9 depicts a printer according to an embodiment of the invention.

The Heteroform printer, as shown in FIG. 9, consists of multiple nozzles mounted on a 3D robotic positioning system. While capable of simultaneous four nozzle droplet deposition, it is also capable of simultaneous droplet and fused deposition. The droplet deposition nozzles are modular, and any combination of droplet deposition materials may be selected. The 3D positioning system itself has a positional resolution of 10 microns, and droplet sizes vary from 50 to 300 microns in width. A fused deposition head, which has been used individually with great reliability but not yet mounted on the multi-nozzle arm, has been shown to create struts of PCL measuring 150 microns across with pores of less than 100 microns.

Four materials have been selected for inclusion in the Heteroform printer, each with specific biological contributions to tissue scaffolds. Suitable materials for heterogeneous deposition include poly-$\epsilon$-caprolactone (PCL), alginate, fibrin, and chitosan, wherein poly-$\epsilon$-caprolactone (PCL) was fused deposited and alginate, fibrin, and chitosan were droplet deposited. Primary considerations for ideal scaffold materials include the mechanical properties, the intrinsic biocompatibility, biodegradability, solvent for inducing degradation, cell attachment, and material-specific biological responses. All of the candidate materials are biocompatible. Table 1 summarizes properties of materials. PCL is extremely rigid; alginate is always structurally weak but diffuses particles of less than 1200 Daltons readily, including gas molecules. Fibrin and chitosan both have a high rate of cell attachment with increased ECM deposition and very steady release profiles respectively.

TABLE 1

Properties of Candidate Materials

| Material | Deposition | Cross-linker | Biodegradable | Cell Attachment | Mech. Properties | Commercial Uses | Solvent | Specific Responses |
|---|---|---|---|---|---|---|---|---|
| PCL | Fused | None | ~2 years | Low | Extremely Rigid | Increasing implant rigidity | Chloroform | Very rigid |
| Alginate | Droplet | Ca++ | ~weeks/months | None unless modified | Weak Hydrogel | Wound packing | Chelating agents | Hydrogel with ready diffusion |
| Fibrin | Droplet | Thrombin | ~weeks | High | Varying | Glue/Sealant | Plasminogen | Increased ECM |
| Chitosan | Droplet | NaOH | ~weeks | High | Varying | Limited | Lysozyme | Steady release profile |

* The mechanical properties and degradation rates of fibrin, alginate, and chitosan vary by concentration of substrate and crosslinker.

The architectural considerations for tissue scaffolds may be divided into the categories of cell attachment, transport, and mechanical properties. Typically, in homogenous deposition, attachment to a substrate is enhanced by increasing the available surface area for attachment or by selecting a material with greater biological affinity. Increasing porosity increases surface area but raises transport issues. If the pores are not interconnected, nutrients and gases will not be able to diffuse through the scaffold. Also, small pores may be occluded as cells proliferate. An alternative to fine porosity control is material selection. For instance, fibroblasts will not attach to alginate, will attach weakly to PCL, and will attach and proliferate on chitosan scaffolds. A heterogeneous deposition option might include a heterogeneously porous structure of PCL with isolated units of chitosan to increase attachment in the scaffold.

To further enhance transport, the authors propose a novel method of mass transport to scaffold interiors, to be tested with the Heteroform printer. It has been suggested that instead of using pores or channels to transport mass between the scaffold interior and exterior, a network of hydrogel be used as a surrogate vascular system. This diffusive network, most likely in the form of thread-like alginate filler running at regular intervals through a scaffold, might allow sufficient mass transport to maintain interior cell populations while preventing cells from clogging the passageway. Particles with molecular weight of less than 1300 Da, such as glucose and oxygen, and stokes radii of less than 1 nm are able to freely diffuse through alginate microspheres.

The Heteroform printer is capable of depositing a very small volume (a droplet of 50 microns in diameter) of growth-factor-bearing material to a precise location. As diffusion is an inverse square law function, there exists the potential to create large concentrations of growth factor within a local region of a scaffold that fall off dramatically with distance. The information necessary to calculate the concentration of growth factor consists of the release profile of the delivery material from the literature and an FEM model of diffusion taking into account a heterogeneous scaffold environment with multiple diffusion constants and a variable perfusion rate.

Figure 10:
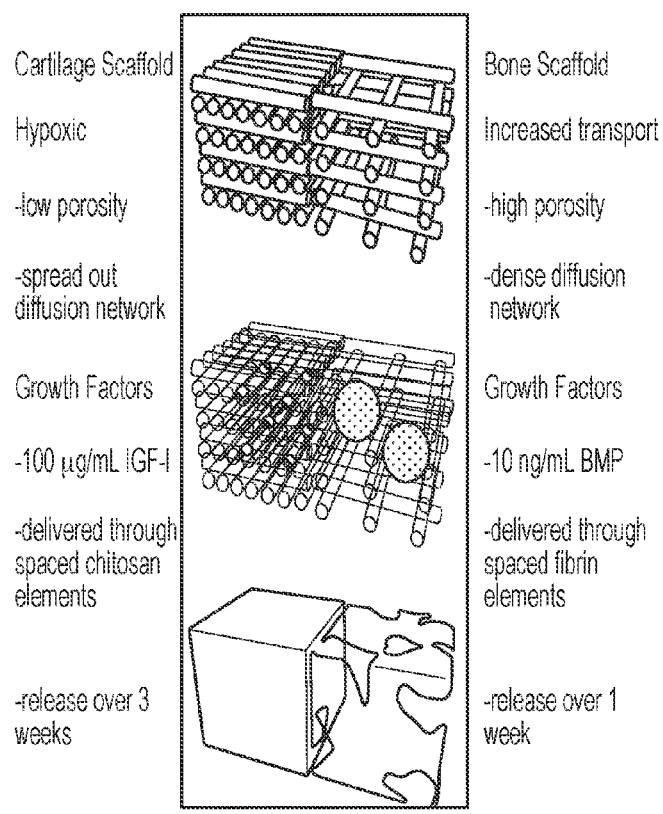
FIG. 10 depicts a scaffold according to an embodiment of the invention.

Combining all of the tools described above allows for the possibility of creating multiple regions optimized for specific cell types within the same scaffold. The ideal combination of parameters to create a tissue interface would be for the each scaffold regions to be conducive to one cell type but hostile to the other. For instance, in designing a scaffold for an interface between bone and cartilage such as in FIG. 10 one could take advantage of the fact that chondrocytes are more tolerant of a hypoxic environment than are osteoblasts by reducing the porosity. Also, growth factors to induce cell proliferation and matrix deposition are known for both osteoblasts and chondrocytes, and release elements could be positioned appropriately.

While the invention has been described in detail and with reference to specific examples thereof, it will be apparent to one skilled in the art that various changes and modifications can be made therein without departing from the spirit and scope thereof.

REFERENCES

[1] Freed, L. E. and G. Vunjak-Novakovic. 1998. Culture of organized cell communities. *Advanced Drug Delivery Reviews*. 33: 15-30.
[2] Shachar, M. and S. Cohen. 2003. Cardiac tissue engineering, ex-vivo: design principles in biomaterials and bioreactors. *Heart Failure Reviews*. 8: 271-276.
[3] Abukawa, H., H. Terai, D. Hannouche, J. P. Vacanti, L. B. Kaban, and M. J. Troulis. 2003. Formation of a mandibular condyle in vitro by tissue engineering. *J Oral Maxillofac Surg*. 61: 94-100.
[4] Grogan, S. P., F. Rieser, V. Winkelmann, S. Berardi, and P. Mainil-Varlet. 2003. A static, closed and scaffold-free bioreactor system that permits chondrogenesis in vitro. *Osteoarthritis and Cartilage*. 11:403-411.
[5] Knazek R A, Gullino P M, Kohler P O, Dedrick R L. Cell culture on artificial capillaries: an approach to tissue growth in vitro. Science 1972; 178: 65-67.
[6] Pg 92. Freshney, I R. Culture of Animal Cells: a manual of basic technique. $4^{th}$ ed. John Wiley & Sons, Inc. New York. 2000.
[7] Takezawa T. A strategy for the development of tissue engineering scaffolds that regulate cell behavior. *Biomaterials* 2003; 24: 2267-2275.
[8] Takezawa T, Yoshizato K. Mass transport via naturally branched scaffolds maintains viability of a reconstituted model of connective tissue. *Tissue Engineering* 1997; 3 (4): 329-343.
[9] Reischmann M, Merz R, Schultz L, Weiss L E. Prototype implementation of an assembly system for tissue engineered constructs. *Electrotechnik und Informationstechnik* 2002; 7/8: 248-252.
[10] Weiss L E, Merz R, Prinz F B, Neplotnik G, Padmanabhan P, Shultz L, Ramaswami K. Shape deposition manufacturing of heterogeneous structures *Journal of Manufacturing Systems* 1997; 16(4): 239-248.
[11] Xiong Z, Yan Y, Wang S, Zhang R, Zhang C. Fabrication of porous scaffolds for bone tissue engineering via low-temperature deposition. *Scripta Materialia* 2002; 46: 771-776.

[12] Yan Y, Xiong Z, Hu Y, Wang S, Zhang R, Zhang C. Layer manufacturing of tissue engineering scaffolds via multi-nozzle deposition. *Materials Letters* 2003; 57: 2623-2628.

[13] Landers R, Mülhaupt R. Desktop manufacturing of complex objects, prototypes and biomedical scaffolds by means of computer-assisted design combined with computer-guided 3D plotting of polymers and reactive oligomers. *Macromol Mater Eng* 2000; 282: 17-21.

[14] Landers R, Mülhaupt R, John H. Desktop manufacturing and biofunctional processing. *Kunststoffe/plast Europe* 2001; 91 (12): 21-23.

[15] Landers R, Hübner U, Schmelzeisen R, Mülhaupt R. Rapid prototyping of scaffolds derived from thermoreversible hydrogels and tailored for applications in tissue engineering. *Biomaterials* 2002; 23: 4437-4447.

[16] Calvert P, O'Kelly J, Souvignier C. Solid freeform fabrication of organic-inorganic hybrid materials. *Materials Science and Engineering* 1998; C6: 167-174.

[17] Vozzi G, Flaim C J, Bianchi F, Ahluwalia A, Bhatia S. Microfabricated PLGA scaffolds: a comparative study for application to tissue engineering. *Materials Science and Engineering* 2002; C20: 43-47.

[18] Vozzi G, Flaim C J, Ahluwalia A, Bhatia S. Fabrication of PLGA scaffolds using soft lithography and microsyringe deposition. *Biomaterials* 2003; 24: 2533-2540.

[19] Ang T H, Sultana F S A, Hutmacher D W, Wong Y S, Fuh J Y H, Mo X M, Loh H T, Burdet E, Teoh S H. Fabrication of 3D chitosan-hydroxyapatite scaffolds using a robotic dispensing system. *Materials Science and Engineering* 2002; C20: 35-42.

[20] Khalil S, Nam J, Sun W. Multi-nozzle Deposition for Construction of 3D Biopolymer Tissue Scaffolds. *Rapid Prototyping Journal* 2005; 11(1): 9-17.

[21] Wang F, Shor L, Darling A, Khalil S, Sun W, Güçeri S, Lau A. Precision Extruding Deposition and Characterization of Cellular Poly-ε-Caprolactone Tissue Scaffolds. *Rapid Prototyping Journal* 2004; 10(1): 4249.

What is claimed is:

1. An artificial tissue comprising an internal mass transport network having a plurality of channels, wherein the internal mass transport network comprises a biodegradable transporting material that is substantially free of suspended cells, and which is simultaneously deposited in a pattern with a scaffold material to form a plurality of layers of the artificial tissue, and wherein the channels are designed to substantially mimic a naturally occurring vascular network, such that the internal mass transport network creates a basic circulatory system within the scaffold, and wherein the internal mass transport network having a plurality of channels comprises the void space remaining after the biodegradable transporting material has biodegraded.

2. The artificial tissue of claim 1, wherein the biodegradable transporting material comprises a hydrogel and the scaffold material comprises a polymer and/or a bioactive glass.

3. The artificial tissue of claim 2, wherein the hydrogel is a member selected from the group consisting of alginate, collagen, chitosan, fibrin, hyaluronic acid, agar, polyethylene glycol and its copolymers, acrylamide-based polymers, acrylic acid-based polymers, and the scaffold material is a member selected from the group consisting of polycaproactone, polyglycolic acid, polylactic acid, polyhydroxybutyrate, polypropylene and their co-polymers, fumarate tricalcium phosphate, and hydroxyapatite.

4. The artificial tissue of claim 1, wherein the biodegradable transporting material is coated with a coating to form at least one coated channel or at least one partially coated channel such that a property of the at least one coated channel or the at least one partially coated channel is different from a property of a channel, wherein the property is selected from the group consisting of selective permeability, diffusivity, cell transport, cell adhesion, hydrophobicity, and a hydrophilicity.

5. The artificial tissue of claim 4, wherein the coating forms at least one barrier to affect cells migration.

6. The artificial tissue of claim 1, wherein the scaffold comprises more than one scaffold material.

7. The artificial tissue of claim 1, further comprising cells in contact with said scaffold.

8. The artificial tissue of claim 1, wherein the artificial tissue further comprises an artificial transpiration circulatory system connected to an outer layer of the artificial tissue, wherein the artificial transpiration circulatory system is adapted to aid circulation within the artificial tissue.

* * * * *